United States Patent
Smolko et al.

(10) Patent No.: US 8,414,923 B2
(45) Date of Patent: Apr. 9, 2013

(54) IMMOBILIZATION OF BIOACTIVE MOLECULES WITHIN A POLYMERIC SUBSTRATE

(76) Inventors: Eduardo Esteban Smolko, Buenos Aires (AR); Eduardo Antonio Lombardo, Buenos Aires (AR); Fabio Martin Lombardo, Buenos Aires (AR); Jorge Héctor Lombardo, Entracque (IT)

(*) Notice: Subject to any disclaimer, the term of this patent is extended or adjusted under 35 U.S.C. 154(b) by 0 days.

(21) Appl. No.: 12/677,865
(22) PCT Filed: Sep. 12, 2008
(86) PCT No.: PCT/IB2008/002368
§ 371 (c)(1), (2), (4) Date: Mar. 12, 2010
(87) PCT Pub. No.: WO2009/034453
PCT Pub. Date: Mar. 19, 2009

(65) Prior Publication Data
US 2011/0217378 A1 Sep. 8, 2011

(30) Foreign Application Priority Data
Sep. 13, 2007 (AR) ................. P070104071

(51) Int. Cl.
*A61K 9/00* (2006.01)

(52) U.S. Cl. .......... 424/484; 424/486; 424/487
(58) Field of Classification Search .......... None
See application file for complete search history.

(56) References Cited

U.S. PATENT DOCUMENTS
6,004,583 A * 12/1999 Plate et al. .......... 424/486
2006/0153919 A1 * 7/2006 Metters et al. .......... 424/486

FOREIGN PATENT DOCUMENTS
EP 08807055.2 1/2012

OTHER PUBLICATIONS

Zhuang et al., Radiation Polymerization and Controlled Drug Release of Polymer Hydrogels with NIPA and NVP, Feb. 2003, Journal of Applied Polymer Science, vol. 88, 724-729.*

* cited by examiner

*Primary Examiner* — Anand Desai
*Assistant Examiner* — Melissa Mercier
(74) *Attorney, Agent, or Firm* — Collen IP; Donald J. Ranft (57) ABSTRACT

A method for the immobilization of bioactive molecules within a polymer substrate to be employed as an oral drug delivery system is provided. A water insoluble carrier matrix can be provided that is water swellable, and biologically active agents can be incorporated. The matrix can be a macromolecular network synthesized by gamma radiation at temperatures between −78 degrees Celsius to a boiling point of a component elected for polymerization.

9 Claims, 2 Drawing Sheets

Glycemia in normal mice, with oral insuline without polymer.

Figure 1:
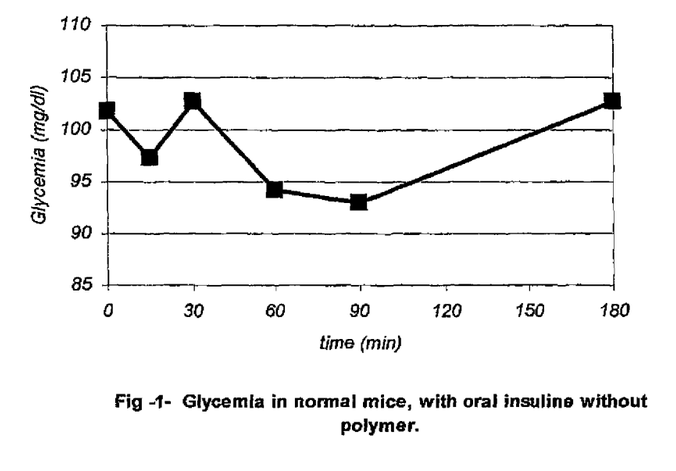

Fig -1- Glycemia in normal mice, with oral insuline without polymer.

Figure 2:
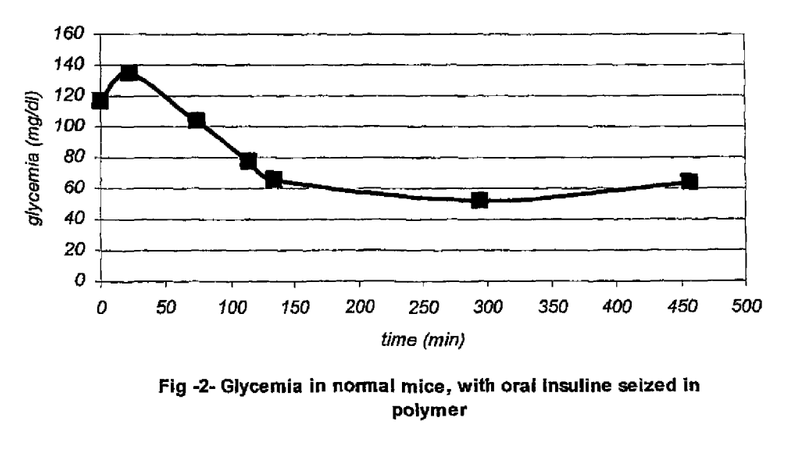

Fig -2- Glycemia in normal mice, with oral insuline seized in polymer

Figure 3:
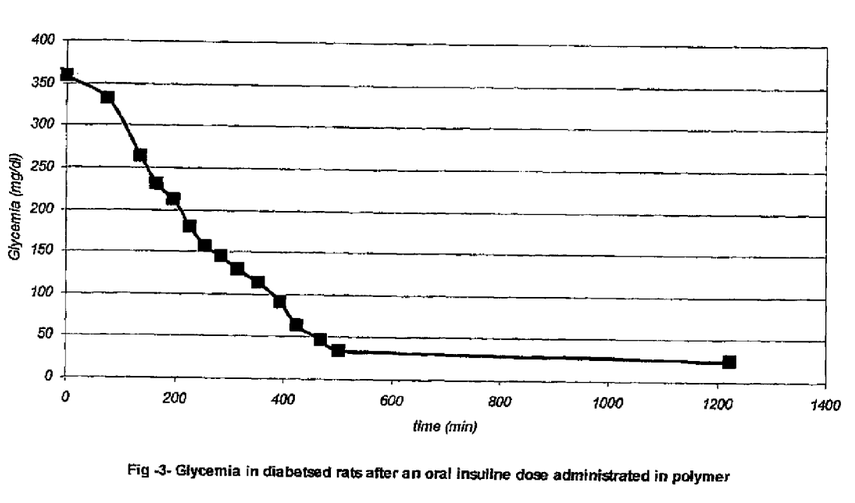
Figure 4:
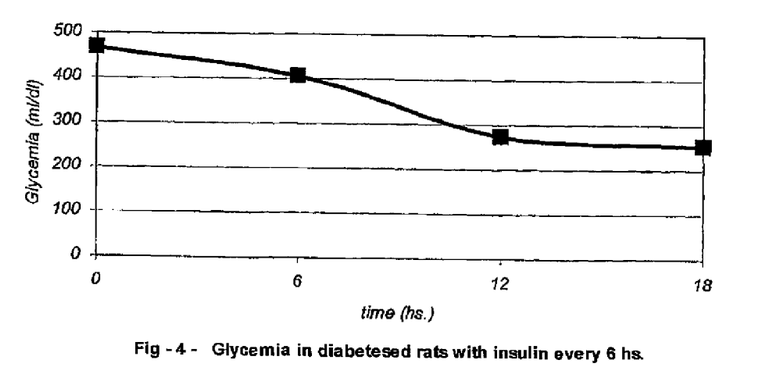

Fig -3- Glycemia in diabetsed rats after an oral insuline dose administrated in polymer Fig -4- Glycemia in diabetesed rats with insulin every 6 hs.

IMMOBILIZATION OF BIOACTIVE MOLECULES WITHIN A POLYMERIC SUBSTRATE

INTRODUCTION

1. Field of the Invention

The present invention describes a technology that allows surpassing the gastric barrier imposed on protein compounds, while acting on the administration rate of bioactive molecules, such as (e.g.) insulin, heparin, antigens, hormones, or the like, particularly insulin.

Under the effect of ionizing radiation, determined monomers (with or without the addition of other chemical compounds) are polymerized modifying their physical state from a liquid into a solid state. If in the monomer it is provided a molecular bioactive drug in suspension or dissolved in aqueous solutions, during the formulation process prior to said ionizing irradiation step, it may be achieved that said drug or drugs considered will remain passively encapsulated (that is, without chemical interaction) within the nanotubules formed during the irradiation process.

The requirements and irradiation doses described in this present invention determine the size, shape, physical characteristics, etc., of the nanotubules which will finally establish the liberation rate of the therein enclosed drug.

The compound having a controlled liberation rate, (retard) comprises a support polymerized by means of radiation (hydrogel).

The compound formed by the hydrogel and the drug enclosed within it (into its nanotubules) has a-very low hydration, hence upon its ingestion by the patient, due to the intrinsic characteristics and structure of said hydrogel (being this the end product of a mixture of hydrogels of different formulation), reaches the stomach without suffering alteration or degradation. Also this hydrogel, neither undergoes structural changes, or the liberation of significant amounts of the drug therein contained, during its stomach's trajectoryv Once it enters into the intestine the drug release starts according to the transit lapse of time, the chosen hydrogel formulation, the amount of drug incorporated, etc. These characteristics are also related to the type of ingestion.

In short, this present invention is proposing a method capable to replace the daily injectable and repeating doses of a drug, by means of an orally administrated product.

The sample product employed to illustrate this instant invention, due to its importance, the availability of the means and the collaboration of clinical experts, it referred to the controlled release of insulin. Introducing said insulin into radio induced polymers, and conducting the clinical tests with mice, rats and dogs, they were obtained surprisingly favorable results.

The final object of this development is obtaining an oral administrated insulin applicable to patients suffering from diabetes Type I (which are those patients in need of one or more daily insulin doses and representing over 60,000,000 persons, world wide) and Type II patients, insulin-dependents.

It has been duly recorded the results and collected data pertaining to continuous experiments, dating several years and related to the incorporation of drugs into radio induced polymers due to the application of electromagnetic and corpuscular ionizing radiation.

Moreover, the market for diabetes treatment drugs amounts to about a gross overall of 15,000,000,000 U$S per annum and it is expected that by year 2011 this turnover will reach the yearly amount of 25,000,000,000 U$S. The proposed alternative according to this patent is not a solution to this disease, but it constitutes a remarkable complement to improve the standard and life quality as per comparison to the actually known drug delivery (insulin) treatments.

In Argentina (the rest of the world has similar values) 7% of its population suffers diabetes, but within this statistic, about 30% are not aware of their illness. One of the characteristics of this disease is that it comes unannounced, that is, without forewarning and it is painless. According to the World Health Organization, at least 143,000,000 people are afflicted by this illness, and a significant escalation to 300,000,000 people is expected by the year 2025. In the developed countries people afflicted by diabetes are mainly of an age in excess of 65 years, while in the developing (or emerging) nations it is prevalent in younger generations, between 45 to 65 years.

The most feared problem is not diabetes as such, but its collateral complications, such as the retinopathies which may end blinding the affected person, renal insufficiency which may end needing dialysis or diabetic neuropathies, which may end with the amputation of the lower limbs, being this in fact the most frequent cause of the non traumatic severance of the lower limbs.

Is also of research interest other bioactive molecules such as heparin, but what is herewith proposed in a first stage: the study of an oral insulin, encapsulated into polymeric nanotubules due to the knowledge and experimental results obtained by this research team, on this subject.

2. Brief Description of Prior Art

It has been recently marketed a new product, named "JUL Exhubeta" (Pfizer) as an only known alternative to the injectable application of insulin in Type I diabetes, which is insulin administered by inhalation with effects similar to the ones of injectable insulin; nevertheless this kind of drug administration is already mentioned as the responsible agent in the production of pulmonary fibrosis, with the additional inconvenience of being a medicine in need of a very good attitude and education from the patient.

The entrapment or encapsulating technology of the antigens in polymers has been also a study motive of study by our team at the DeutschesKrebsForschungZentrum (DKFZ) of Heidelberg—Germany, particularly for the HPV (HUMAN PAPILOMA VIRUS) and more particularly addressed to the production of oral vaccines; while this technology would be applicable to many other viruses, proteins, hormones of medical and agriculture and cattle rearing.

BRIEF DESCRIPTION OF THIS INVENTION

The method for the introduction of bioactive molecules in a polymeric substratum resistant to the stomach acids, to be employed as a delayed release oral medication, particularly insulin molecules, is characterized by comprehending the following steps:

a) To mix at least a monomer suitable to be polymerized by a ionizing radiation, with at least an aqueous solution of bioactive molecules;

b) To place the thus obtained mixture of step (a) into a container permeable to said ionizing radiation;

c) Submit said container to a flow of ionizing radiation at a dose range from 0.1 kGy up to 50 kGy, specially at a dose between 5 and 30 kGy, capable to polymerize all the monomer, obtaining within the container a polymer resistant to the stomach acids containing into its nanotubules the bioactive molecules;

d) Withdraw the thus obtained polymer in step (c) fractioning it batches with a size range between 1 mm×1 mm×1 mm up to 8 mm×8 mm×8 mm, capable to form part of the delayed drug delivery oral medication.

In a preferable construction, the method of this invention is characterized because in step (a) said at least one monomer is at least an acrylic monomer, of the family of the alkyl methacrylates and acrylates, such as hydroxiethylmethacrylate (HEMA), forming the macromolecular network.

In other constructions, the method of this invention is characterized because in step (a) said at least one monomer is mixed with additive substances providing protection against the radiolysis, such as antirad substances, free radical substractors, chain transference substances (for example, glycerin). In a family of preferred embodiments, the aqueous solution of a bioactive substance is an insulin watery solution.

Is an integral part of this instant invention, as a secondary object, the medicine thus obtained, which active substance is found within the inner part of the fractions or parts thereof, resistant to the action of the gastric or stomach acids and which delaying action is a function of the parameters employed in said obtained method.

Properties and Disadvantages of the Action of Administrating Injectable Insulin

The insulin is a hormone essential in the carbohydrates metabolism. Said hormone is produced by the pancreas and it is secreted within the portal circulation to be liberated by the liver wherein it performs its main metabolic effect. The insulin reaches the systemic circulation enabling the glucose to be captured by the insulin dependent peripheral tissues (muscle, kidney).

Insulin plays a mayor role in diabetes, which is a progressive illness caused by the combination of a relative efficiency in the insulin production and/or a resistance of the peripheral tissues to insulin. Ambient or genetic factors (lack of physical exercise, obesity) apparently play a significant roll in the diabetes pathology.

There are patients suffering from diabetes which are insulin dependent (Mellitus Diabetes Type I), or not insulin dependent (Mellitus Diabetes Type II).

People suffering from diabetes Type II, (also known as elderly diabetics), have a metabolic disorder resulting in the incapacity of the body to produce or to employ adequately it's insulin. The most advanced cases within this type of patients require exogenous insulin supplemental to its own endogenous insulin.

Patients suffering from the first stages of diabetes Type II are typically provided with non insulin oral hypoglycemiants which are able to stimulate the liberation of insulin or other products that can increase insulin sensitivity of peripheral tissues. When the illness continues progressing, as it happens in most cases, the pancreatic cells producing insulin degenerate and die, which results in a complete loss in the insulin production, consequence of which the patient requires multiple insulin subcutaneous injections.

The subcutaneous insulin injections do not reproduce the physiological conditions of insulin in liver and in the systemic circulation. In healthy individuals insulin is secreted directly in the portal hepatic system, being the liver the first site of action. Instead, by means of subcutaneous application, it is exposed to high insulin concentrations in comparison to the systemic concentration.

Physiologically, insulin is rapidly secreted as a metabolic reply to the glucose concentration in the bloodstream following the food ingestion.

Injected insulin is released in the systemic circulation after a lapse of time determined by the dissolution and diffusion time in the area of application of the injection and it is independent of said application area and of the glucose concentration in blood.

Hypoglycemia may often take place when insulin is administered by means of an injection, due to the fact that the injected insulin is not in coordination with the body's secreted insulin.

In opposition to the injected insulin, orally administered insulin is released directly to the liver and being this the first site of action through portal circulation.

The insulin released into the liver restrains the production of hepatic glucose, the main contribution to the hyperglycemia, in Type II diabetes.

Theoretically the oral insulin would need less insulin per dose in order to produce the desired effect.

Also, the use of oral insulin does not produce peaks in the systemic circulation such as the ones produced by injectable insulin, reducing the risk of a sudden decrease of glycemia.

The effect of the lower level of glucose in blood, given by insulin, facilitates the capture of glucose after the union of insulin to the receptors to be found in the muscle and fat tissue cells, and to the simultaneous inhibition of the glucose production from the liver.

The average life of insulin in the bloodstream is only of a few minutes. Because of this, the result in time of an insulin preparation is determined only by its absorption characteristics. This mechanism is influenced by the administered insulin concentration as well as by the administration means and the zone or area of the body on which it is applied. An average action profile after subcutaneous injection indicates:

Initial: within the first half hour;
Maximum: between 1.5 y 3.5 hours;
Duration: approximately 7-8 hours after.

These characteristics are observed in children as well as adolescents. The maximum injected insulin plasmatic concentration is attained within 1.5 and 2.5 hours after the subcutaneous administration.

Drug Distribution:

No significant bond to plasmatic proteins has been observed, except the case of circulating insulin antibodies.

Metabolism:

It has been reported that human insulin is degraded by protease insulin or the insulin degradation enzyme system. Also probably by the disulphide isomerase's protein. It has been identified a number of lyses sites placed along the human insulin molecule. None of the metabolites produced in this lyses are active.

The average time life of injected insulin is determined by the absorption range of the subcutaneous tissue. The average life time (t½) is, notwithstanding not more than a measure of the insulin elimination rate, a measure of the absorption (insulin in bloodstream has a t½ value of a few minutes). Clinical studies have indicated a t½ of about 2-5 hours. The pharmacokinetic profile is similar in children and adolescents in comparison to that of adults.

Dosage and Administration:

Dosage is customized and determined by the professional attending the patient in accordance with its needs. The daily average insulin requirements treating diabetes in diabetic patients Type I vary between 0.5 and 1.0 IU/kg, according to each patient. Nevertheless, in pre-pubescent patients usually varies between 0.7 and 1.0 IU/kg, but the dose may be even lower during the partial remission period. In an insulin-resistance situation, for instance during puberty or due to obesity, the daily requirements could be significantly greater. The initial dose in diabetic patients Type II is often lower, for instance, 0.3 and 0.6 IU/kg/per day. In patients with mellitus diabetes, optimized metabolic control retards the beginning and progression of the delayed complications. For this reason, it is suggested to perform a thorough metabolic control, including glucose control. In advanced age patients, the primary objective could be to alleviate symptoms and to avoid hypoglycemic incidents.

Insulin is usually administered by means of subcutaneous injections in the abdominal wall. It may be also injected in the thigh, the gluteus and the deltoid region. The subcutaneous injection in the abdominal wall ensures a faster absorption than those of other injections sites. The injection in a skin fold, minimizes the risks of an intramuscular injection. Only a human insulin solution is appropriate for its intravenous administration. It should be applied only by a physician or qualified person. The injection sites or places should rotate within the anatomical region, in order to avoid lipodistrophya. Every injection must be followed, within the next 30 minutes, by food ingestion containing carbohydrates.

Precautions:

Inadequate dosage or treatment discontinuity, especially in the Type I diabetes, may result in hyperglycemia and diabetic ketoacidosis. Generally the first hyperglycemia symptoms start gradually, along a period lasting from hours to days. Said symptoms includes thirst, increase or urinary frequency, nausea, vomits, drowsiness, reddened dry skin, mouth dryness, loss of appetite, as well as breath tainted with acetone.

In diabetes Type I, the untreated hyperglycemia events will eventually lead to diabetic ketoacidosis which may be potentially lethal. The concomitant pathologies, mainly infections and fevers, usually increase the patient's insulin requirements.

Deficiencies in renal or hepatic operation may reduce insulin requirements. If patients increase their physical activity or modify their usual diet, it may be necessary to modify insulin dose.

Interactions:

It is known that certain drugs interact with glucose metabolism. The physician must take into account the possible interactions.

The following substances may reduce insulin requirements:

Oral hypoglycemiants, octreoctids, monoamineoxidase inhibitors, non selective beta blocking agents, angiotensine-converting enzyme inhibitors, salicylates, alcohol, sulphonamide antibiotics, anabolic steroids, quinine, quinidine and alpha-adrenergic blocking agents.

The following substances may increase insulin requirements:

Oral contraceptives, tiazydes, glucocorticoids, thyroid hormones, simpaticomimetics, growth hormones, diazo oxides, asparaginase and nicotinic acid. The beta blocking agents may mask hypoglycemic symptoms and delay the recovery of a hypoglycemia. Alcohol may intensify and extend the hypoglycemic effect of insulin.

Pregnancy and Milk-Fed Babies:

There are no restrictions to insulin treatment during pregnancy, since insulin does not cross the placenta barrier. Untreated mellitus diabetes constitutes a risk for the intrauterine development, during pregnancy. Therefore the diabetes treatment must be continued during pregnancy. Both, untreated hypoglycemia as well as untreated hyperglycemia, which may take place due to inadequate control of the diabetes treatment, increases risk of malformations and death within the uterus. It is suggested the strict control of the diabetic pregnant woman along all the pregnancy stages, and when pregnancy is planned. Insulin requirements usually diminish during pregnancy's first quarter, and they increase in the following second and third quarters. After childbirth, insulin requirements reset rapidly to their pre-pregnancy levels.

Effects on Driving and Tool Machinery Usage:

The capability of the patient to pay attention and to react promptly may lessen as result of the hypoglycemia. This may constitute a risk under situations in which said capacity is of a particular importance, such as, for instance, driving a vehicle or operating tool machinery. Patients should be forewarned to take precautions in order to avoid hypoglycemia while driving. This is of particular relevance in patients having little or no awareness about signs announcing a hypoglycemic episode, or that suffer frequent hypoglycemia episodes. Under these circumstances it may be safer to consider not driving.

Adverse Effects:

The most frequent adverse effects, in patients under insulin treatment, are the changes in the level of glucose in blood.

Nutrition and Metabolism Disorders:

Changes in the levels of glucose in the blood frequency ($<1/1000$).

Hypoglycemia:

The hypoglycemia symptoms generally take place suddenly. They may include cold sudoration, pallor and cold skin, fatigue, nervous state, anxiety, tiredness or general weakness, confusion, difficulties in concentration, sleepiness, excessive hunger, and modifications in the vision, headaches, nausea and palpitations. Serious hypoglycemic episodes may lead to the loss of consciousness and or convulsions and may result in a temporary or permanent cerebral malfunction, or even death.

Hyperglycemia:

Usually the first hyperglycemia symptoms appear gradually, after a period of hours or days, and they include: thirst, increase in the urinary frequency, nausea, vomits, drowsiness, reddening dry skin, dryness in the mouth, loss of appetite, as well as breath tainted with acetone. In diabetes Type I, the untreated hyperglycemia events will eventually lead to diabetic ketoacidosis which may be potentially lethal.

Vision Disorders:

Anomalies of frequency refraction ($<1/10,000$):

Refraction anomalies may take place after the beginning of the insulin administration. These symptoms are of a transitory nature.

Skin and Subcutaneous Tissue Disorders:

Lipostophosis Frequency ($<1/10,000$):

In the injection place it may take place lipostophosis as a consequence of applying in the same area subsequent injections.

General Disorders:

Local Hypersensitivity:

Frequency ($<1/10,000$): During treatment with insulin it can take place local hypersensitivity reactions (skin reddening, inflammation and itching in the application place) and these reactions are usually transitory. They disappear under a continuous treatment.

Generalized Hypersensitivity: Frequency ($<1/10,000$):

Generalized hypersensitivity reactions may include: generalized skin rash, itching, sudoration, gastrointestinal indisposition, angioneurotic edema, breathing difficulties and palpitations.

ADVANTAGES AND OBJECTIVES OF THIS INVENTION

It is an objective of this present invention a method for the introduction of bioactive molecules into a polymeric substrate resistant to stomach acids, for its employ as a controlled liberation oral medicine.

It is also an objective of this invention a method for the introduction of bioactive molecules (being said molecules, insulin molecules) into a polymeric substrate resistant to the stomach acids, suitable to be used as an oral medication having a controlled (retarded) delivery.

Another objective of this invention is obtaining a medication having a prolonged release time for its bioactive molecules, being those molecules insulin molecules, and being them directly delivered into the liver, as a first action site, through portal circulation.

An additional objective of this invention is that this oral medication of prolonged insulin drug release in the liver, is capable to restrain heptic glucose production, which is the main cause for hyperglycemia in Type II diabetes.

Another objective of this invention is the production of an oral medication capable to perform a retarded drug liberation by means of which liberated insulin does not produce peaks in the systemic circulation, as opposed to what happens when injected insulin is administered, thus reducing the risks of a sudden glycemia decrease.

It is a last object of this invention, the development of a prolonged drug release oral medication, by means of which it is needed a less insulin provision to produce the same effect that the one obtained by injected insulin.

THIS INVENTION DESCRIPTED THROUGH AN EXAMPLE

The advantages above briefly explained, to which its users and people trained in this Art may add many more, is hereinafter described, through a preferred experiment in laboratory animals, and depicted schematically in the enclosed drawings, with the given express explanation that indeed this is only a preferred example, and it must not be considered in any way, limitative in its character, or otherwise limiting the patent scope, since it is merely explicative and illustrative of the basic conception on which the invention is grounded, being the actual broad scope of this invention given by the herewith enclosed claims.

Pharmacological Properties of Insulin:

The hypoglycemiant effect pertaining to insulin is given by its absorption facilitation of glucose by muscle and fat tissue cells, and to the simultaneous inhibition of the liver glucose production.

Ionizing Radiation and Polymers:

The exposure to ionizing radiation requires the previous assessment of the absorbed dose and the speed of the absorbed dose. These variables depend on the elected radiation facility. A given particular facility and will allow to determine the best radiation conditions. The development performed by the authors of this invention allowed the creation of diverse products, radiating in dose comprehended in the sterilization by radiation range (doses not larger than 25 kGy), in terms of a few hours lapse.

In the case of the introduction of insulin into de radio-induced polymers, the following has been performed:

The best parameters for said insulin incorporation were determined.

Preparations covered by this invention may incorporate insulin of a natural origin or synthetic insulin, particularly the ones obtained through genetic-engineering process; Insulin is introduced into the final product by means of at least a homogenous mixture, along with the solvents, principally water, and protective substances such as glycerin and monomers. The mix is then fractioned or divided and introduced under a controlled environment, in polymeric containers. Those containers have been treated by ionizing radiations, and finally obtaining a product ready for its use.

Biosynthetic human insulin is incorporated under the form of watery solutions, completely mixable with the rest of the components. The latter have been mainly formed by acrylic monomers, alkyl methacrylates and acrylates, specifically hydroxiethylmethacrylate (HEMA), constituting a macromolecular net. Also was added radiolysis protecting substances such as antirad substances, free radical substractors and chain transference agents such as glycerin? These substances, in adequate percentage quantities, were put under a radio induced polymerization process, and to that aim, it has been irradiated with high energy radiation, such as gamma rays of cobalt 60 radioisotope.

The polymers employed were acrylic derivates which, when put under ionization radiations, have the property of undergoing chemical reactions giving origin to large covalent macromolecular formations.

Besides adjusting the product's composition, it was also necessary to establish the best process temperature, the materials for the conformation of the final product geometry and the external conditions of the resulting compound in relation to the atmospheric parameters: vacuum media or controlled gaseous media.

The ionization radiations that can be employed are not only the ones above mentioned. They also include all of those whose physical properties are equivalent and can perform free radicals formations that can give origin to covalent molecular structures. For this objective, we can consider for example X-rays coming from different sources, with electron beam energies ranging from 0.1 to 10 MeV. Still more, we can also include other energy sources, such as ultraviolet rays, or other accelerated particles such as those issued by ion accelerating devices.

Irradiation processes are performed under a strict control of the irradiation variables. This includes especially the temperature level during the whole term of the transformation process. This invention includes all the processes performed under temperatures ranking from −78 Celsius degrees up to boiling point of the components elected for said polymerization.

The absorbed doses of ionization radiations are in a range within 0.1 kGy up to 50 kGy, and more specifically in a 5 to 30 kGy range.

Protection Provided by Glycerin to the Free Radicals Formation.

The proposed method foresee the introduction of glycerin acting as a protective agent in the radio synthesis process, as well as of any other component introduced into the initial preparation for this same purpose, with a proportion equal or less than 35% in weight.

Synthesis of Hydrogels with Alkyl methacrylates and Alkyl acrylates.

The development of insulin preparations will have, especially incorporated into their molecular compounds, alkyl acrylates and alkyl methacrylates chains. More specifically 2-hydroxiethyl methacrylates (HEMA).

Produced Polymer (with the Drug Incorporated) Partition, in Different Fraction Sizes, as to Ensure the Drug Release Under Simile Biological Conditions of that of an Ingested Medicine:

Studies were carried out with fractions comprehended from 0.1×0.1×0.1 cm to 0.8×0.8×08 cm.

Insulin Employed in the Tests:

Product: Actrapid®HM NovoLei® 100 IU/ml

Human Soluble Insulin

Composition:

Biosynthetic human insulin (origin recombinant ADN, produced from *Saccharomyces Cerevisiae*) 100 IU/ml.

1 IU (International Unity) corresponds to 0.035 mg of anhydrous human insulin.

Excipients: Zinc Chloride, glycerol, metacresol, Sodium hydroxide, Chloridic acid, and water suitable for injections.

The irradiation conditions ensuring the best quality of the final product has been described.

Its release or liberation under laboratory conditions and in laboratory animals has been studied.

Bioavailability in laboratory animals, has been studied.

Laboratory experimental pharmacological steps are included. The determination of glycemia in blood is performed employing the following apparatus:

Specifications:
Measuring type device: Accu-Chek Active
Measuring range: 10-600 mg/dL
Size of sampling test: 1 µL
Measurement time: Approximately 5 seconds
Memory size: 200 glucose values in blood with time and date
Construction: Portable
Depth of the puncture device: 0.80; 0.95; 1.10; 1.25; 1.40; 1.55; 1.70; 1.85; 2.00; 2.15; 2.30 mm.

Example 1

Experiments Carried On for Oral Insulin Administration Without Been Seized in Polymer In Table 1 are shown the results of glycemia values obtained in 4 groups of 5 BALB/c mice each 0.4 IU/kg of insulin were orally administered in a solution. The measured values listed in the table are shown averaged in FIG. 1.

30 to 75 minutes after its administration, it may be observed a slight diminution of glycemia in mice.

TABLE 1

| time(min) | Group 1 (mg/dl) | Group 2 (mg/dl) | Group 3 (mg/dl) | Group 4 (mg/dl) |
|---|---|---|---|---|
| 0 | 100 | 100 | 102 | 105 |
| 15 | 98 | 97 | 96 | 98 |
| 30 | 101 | 102 | 103 | 105 |
| 60 | 90 | 93 | 98 | 96 |
| 90 | 93 | 95 | 90 | 94 |
| 180 | 104 | 102 | 105 | 100 |

GLYCEMIA as a function of time, averaged in four groups of BALB/c mice (five mice in each group), to which oral insulin solution (4 IU/kg) was administered (insulin without been seized into polymer).

Example 2

Control of Oral Insulin Incorporated into a Polymer in Normal Mice

This result is shown Table 2 where Glycemia (in mg/dl) was measured in BALB/c mice, 22 g weight (7 groups of mice of 3 mice each). 4 IU/kg of oral immobilized in polymer insulin has been administered along with 100 mg of food, to facilitate its ingestion. In FIG. 2 it may be appreciated that the minimum occurrence happens at 300 minutes and a diminution of glycemia from minute 22 to minute 294 after the insulin administration.

TABLE 2

| Time (min) | Group 1 (mg/dl) | Group 2 (mg/dl) | Group 3 (mg/dl) | Group 4 (mg/dl) | Group 5 (mg/dl) | Group 6 (mg/dl) | Group 7 (mg/dl) |
|---|---|---|---|---|---|---|---|
| 0 | 118 | 120 | 125 | 110 | 108 | 123 | 110 |
| 22 | 142 | 130 | 138 | 129 | 137 | 136 | 128 |
| 74 | 104 | 105 | 109 | 100 | 108 | 99 | 101 |
| 114 | 78 | 70 | 76 | 81 | 82 | 74 | 82 |
| 134 | 72 | 68 | 62 | 63 | 64 | 60 | 69 |
| 294 | 51 | 50 | 49 | 58 | 53 | 54 | 49 |
| 457 | 60 | 61 | 63 | 69 | 64 | 62 | 66 |

GLYCEMIA as a function of time, averaged in seven groups of BALB/c mice (three mice in each group), to which 4 IU/kg of immobilized insulin in polymer was administered orally along with 100 mg of food.

Example 3

Oral Administered Insulin Control in Diabetic Rats

At Table 3 (parts 1, 2 and 3) it is shown the glycemia (in mg/dl) as a function of time for 20 Wistar rats in which diabetes has been induced with streptozotozine (STZ). In order to induce diabetes it was administered to each rat of 250 g in weight, 60 mg/kg of (STZ). Insulin (4 IU/kg) was administered orally with food in a polymer pellet.

In FIG. 3 it may be followed that basal glycemia descends from an initial higher level to a level significantly lower after 6 hours and then it is maintained at this lower level for other additional 14 hours.

TABLE 3

(part 1).

| Time (min) | Group 1 (mg/dl) | Group 2 (mg/dl) | Group 3 (mg/dl) | Group 4 (mg/dl) | Group 5 (mg/dl) | Group 6 (mg/dl) |
|---|---|---|---|---|---|---|
| 0 | 341 | 346 | 355 | 359 | 359 | 370 |
| 75 | 295 | 302 | 290 | 305 | 310 | 320 |
| 135 | 232 | 245 | 240 | 250 | 253 | 255 |
| 165 | 198 | 210 | 224 | 210 | 220 | 225 |
| 195 | 213 | 205 | 214 | 207 | 207 | 210 |
| 225 | 162 | 170 | 160 | 168 | 179 | 185 |
| 255 | 150 | 145 | 155 | 143 | 148 | 155 |
| 285 | 140 | 137 | 135 | 127 | 139 | 145 |
| 315 | 115 | 110 | 120 | 112 | 121 | 130 |
| 355 | 84 | 89 | 90 | 97 | 110 | 110 |
| 395 | 50 | 45 | 59 | 74 | 82 | 80 |
| 425 | 47 | 40 | 46 | 45 | 52 | 45 |
| 470 | 36 | 30 | 30 | 34 | 46 | 33 |
| 503 | 22 | 27 | 19 | 25 | 37 | 29 |
| 1223 | 15 | 17 | 16 | 22 | 25 | 18 |

GLYCEMIA as a function of time in individual Wistar rats (each group one rat) in which diabetes was induced with streptozotocin (60 mg/kg STZ) and orally with food administered 4 IU/kg insulin immobilized in polymer.

TABLE 3

(part 2).

| Time (min) | Group 7 (mg/dl) | Group 8 (mg/dl) | Group 9 (mg/dl) | Group 10 (mg/dl) | Group 11 (mg/dl) | Group 12 (mg/dl) |
|---|---|---|---|---|---|---|
| 0 | 345 | 369 | 358 | 360 | 371 | 359 |
| 75 | 320 | 346 | 339 | 340 | 345 | 349 |
| 135 | 270 | 270 | 267 | 270 | 270 | 268 |
| 165 | 250 | 235 | 235 | 234 | 238 | 234 |
| 195 | 215 | 220 | 215 | 210 | 211 | 213 |
| 225 | 185 | 185 | 185 | 186 | 179 | 184 |

TABLE 3-continued (part 2).

| Time (min) | Group 7 (mg/dl) | Group 8 (mg/dl) | Group 9 (mg/dl) | Group 10 (mg/dl) | Group 11 (mg/dl) | Group 12 (mg/dl) |
|---|---|---|---|---|---|---|
| 255 | 155 | 148 | 153 | 154 | 154 | 157 |
| 285 | 146 | 140 | 145 | 143 | 147 | 148 |
| 315 | 135 | 121 | 129 | 132 | 131 | 130 |
| 355 | 126 | 115 | 115 | 119 | 114 | 116 |
| 395 | 93 | 79 | 98 | 97 | 98 | 95 |
| 425 | 72 | 54 | 58 | 59 | 57 | 60 |
| 470 | 53 | 38 | 42 | 44 | 43 | 41 |
| 503 | 39 | 29 | 29 | 30 | 28 | 31 |
| 1223 | 24 | 16 | 19 | 28 | 25 | 24 |

TABLE 3

(part 3)

| Time (min) | Group 13 (mg/dl) | Group 14 (mg/dl) | Group15 (mg/dl) | Gorup16 (mg/dl) | Group17 (mg/dl) | Group 18 (mg/dl) | Group19 (mg/dl) | Group20 (mg/dl) |
|---|---|---|---|---|---|---|---|---|
| 0 | 353 | 361 | 380 | 364 | 358 | 357 | 354 | 362 |
| 75 | 345 | 342 | 341 | 345 | 347 | 350 | 348 | 347 |
| 135 | 272 | 269 | 270 | 273 | 280 | 281 | 276 | 271 |
| 165 | 240 | 241 | 235 | 238 | 239 | 237 | 240 | 236 |
| 195 | 214 | 212 | 216 | 220 | 209 | 207 | 215 | 214 |
| 225 | 189 | 182 | 187 | 186 | 190 | 183 | 178 | 186 |
| 255 | 160 | 157 | 158 | 159 | 181 | 170 | 168 | 170 |
| 285 | 150 | 149 | 148 | 142 | 157 | 164 | 158 | 145 |
| 315 | 131 | 134 | 140 | 137 | 140 | 142 | 139 | 132 |
| 355 | 120 | 119 | 120 | 119 | 125 | 128 | 130 | 128 |
| 395 | 99 | 105 | 115 | 109 | 107 | 104 | 115 | 110 |
| 425 | 72 | 71 | 76 | 79 | 74 | 71 | 90 | 89 |
| 470 | 49 | 48 | 50 | 60 | 57 | 54 | 72 | 68 |
| 503 | 35 | 34 | 32 | 45 | 41 | 40 | 55 | 45 |
| 1223 | 30 | 28 | 27 | 31 | 28 | 31 | 35 | 31 |

Example 4

FIG. 4 shows how glycemia as function of time averaged for four groups of diabetic rats of three Wistar rat each one, to which oral insulin was administered simultaneously with food each 6 hs. (Units indicated in mg/dl).

The mice were diabetized with streptozotocine (STZ). It was administered 60 mg/kg of STZ to get a diabetized mouse with a weight of 250 g 4 IU/kg of insulin was administered orally in polymer pellets in 6 h intervals, along with the ingestion of food. It has been observed a diminution of glycemia after the insulin ingestion.

TABLE 4

| Time (h) | Group 1 (mg/dl) | Group 2 (mg/dl) | Group 3 (mg/dl) | Group 4 (mg/dl) |
|---|---|---|---|---|
| 0 | 470 | 469 | 459 | 472 |
| 6 | 408 | 410 | 402 | 398 |
| 12 | 265 | 268 | 282 | 279 |
| 18 | 252 | 254 | 256 | 249 |

GLYCEMIA as a function of time, averaged in four groups of diabetic rats (three rats each in each group), to which oral insulin immobilized in polymer, was administered simultaneously with food every 6 hours.

Example 5

Experience In Vitro (Units Indicated in mg/dl).
Average Result of 3 Experiments

5 IU of insulin incorporated into a polymer has been introduced in 1 ml of a solution with pH 2 during 15 minutes. After this, this same material was placed in solutions of pH 7±0.2 (1 ml) and it was performed successive incubations and injections every 15 minutes (the employed volume in all cases was of 1 ml)

Note: The remaining polymer insulin determination was performed alter 19 successive washing operations giving the following results: insulin: 33325 IU/ml. Employed Method: quimioluminiscent assay.

Example 6

Innocuousness Experiments

To determine the innocuousness of the polymer it was performed subcutaneous implants into mice BALB/c.

5 (five) subcutaneous lateral or side implants of the obtained polymer were performed by means of:
  a) HEMA (Hydroxiethylmethacrylate), 50%, glycerin 10%, water 40%;
  b) HEMA (Hydroxiethylmethacrylate), 60%, glycerin 10%, water 30%;
  c) HEMA (Hydroxiethylmethacrylate), 80%, glycerin 10%, water 10%.

It has been observed clinically during two months. After this the mice were sacrificed and the histopathologycal studies were performed, which did not show any pathological or immune reaction.

We claim:
1. A method for the immobilization of bioactive molecules within a polymer substrate to be employed as an oral drug delivery system, comprising:
  providing a water insoluble carrier matrix that is water swellable; and
  incorporating biologically active agents, where the matrix is a macromolecular network synthesized by gamma radiation at temperatures between −78 degrees Celsius to a boiling point of a component elected for polymerization;

wherein the polymer substrate is a hydrogel; wherein the hydrogel is Drug Delivery System is an aqueous solution containing the bioactive molecules, mixed with the monomer components of the matrix and free radical scavengers.

2. The method according to claim 1, where the macromolecular network obtained after the radiation treatment is a porous substrate comprising a homopolymer or a copolymer prepared from one or more monomers selected from the group consisting of alkyl-methacrylates and acrylates.

3. The method according to claim 1, where the radiation treatment is from gamma radiation sources in a dose range from 0.1 kGy to 50 kGy (kiloGray).

4. The method according to claim 1 where the radiation treatment is from electron beams with energy between 0.1 MeV and 10 MeV.

5. The method according to claim 4, where the radiation treatment is from radiation sources in a dose range from 0.1 kGy to 50 kGy (kiloGray).

6. The method according to claim 1, where the temperature of the radiation treatments is at glass state temperature.

7. The method according to claim 1, where the bioactive molecule is insulin and the free radical scavengers is glycerin.

8. The method according to claim 3, where the radiation treatment is from gamma radiation sources in a dose range from 5 to 30 kGy.

9. The method according to claim 5, where the radiation treatment is from radiation sources in a dose range from 5 to 30 kGy.

* * * * *

UNITED STATES PATENT AND TRADEMARK OFFICE
CERTIFICATE OF CORRECTION

| | | |
|---|---|---|
| PATENT NO. | : 8,414,923 B2 | Page 1 of 1 |
| APPLICATION NO. | : 12/677865 | |
| DATED | : April 9, 2013 | |
| INVENTOR(S) | : Smolko et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 182 days.

Signed and Sealed this
Seventeenth Day of February, 2015

Michelle K. Lee
*Deputy Director of the United States Patent and Trademark Office*